United States Patent [19]
Hirsch

[11] Patent Number: 5,190,727
[45] Date of Patent: Mar. 2, 1993

[54] DEVICE FOR MOVING AND POSITIONING PIPETTE TRAYS IN AN ANALYZER

[75] Inventor: Alexander Hirsch, Stuttgart, Fed. Rep. of Germany

[73] Assignee: Eastman Kodak Company, Rochester, N.Y.

[21] Appl. No.: 732,250

[22] Filed: Jul. 18, 1991

[51] Int. Cl.⁵ .................... G01N 21/01; G01N 35/02; G01N 1/14
[52] U.S. Cl. ........................ 422/67; 422/63; 422/64; 422/65; 422/100; 436/49; 73/864.01; 73/864.14; 206/562
[58] Field of Search ........... 73/863.01, 863.32, 864.01, 73/864.14; 422/63–67, 99, 100, 104; 436/43, 180, 49; 206/562

[56] References Cited

U.S. PATENT DOCUMENTS

| | | | |
|---|---|---|---|
| 3,832,135 | 8/1974 | Drozdowski et al. | 422/65 X |
| 4,130,978 | 12/1978 | Cohen | 206/562 X |
| 4,287,155 | 9/1981 | Tersteeg et al. | 422/100 X |
| 4,349,109 | 9/1982 | Scordato et al. | 206/562 |
| 4,478,094 | 10/1984 | Salomaa et al. | 73/863.32 |
| 4,824,641 | 4/1989 | Williams | 422/100 |
| 4,936,152 | 6/1990 | Aldred | 73/863.32 |
| 5,008,082 | 4/1991 | Shaw | 422/100 X |

FOREIGN PATENT DOCUMENTS 1921302 11/1969 Fed. Rep. of Germany .

Primary Examiner—James C. Housel
Assistant Examiner—Arlen Soderquist
Attorney, Agent, or Firm—Dana M. Schmidt

[57] ABSTRACT

A device for translatorily moving a plate-shaped pipette tray to the processing station of an analyzer for alignment therein. The pipette tray which frictionally rests on a continuous movement device is thereby moved up to a stop member and roughly aligned. A sensor cooperates with an encoding bar formed on the pipette tray and by moving the pipette tray back by a stepper motor exactly aligns the pipettes in their processing station.

15 Claims, 5 Drawing Sheets

DEVICE FOR MOVING AND POSITIONING PIPETTE TRAYS IN AN ANALYZER

FIELD OF THE INVENTION

The present invention relates to a device for translatorily moving a plate shaped pipette tray equipped with pipettes arranged in the direction of tray movement to the processing station of an analyzer for alignment therein.

BACKGROUND OF THE INVENTION

An analyzer is known from DE-A-19 21 302 in which trays equipped with cuvettes are moved along a feed path and past a processing station. The trays are provided with slots cooperating with a feed mechanism. Also a mechanical latching means engages with said slots in order to fix a cuvette exactly in the processing station. Due to its many mechanical components, this known analyzer is of a complex design and operates awkwardly.

More specifically, the problem addressed by the invention centers around tolerances of the tray and of the probe that has to pick up pipette tips in the tray. In order for the tray to be an inexpensive disposable, it is necessary that the tips be carried in apertures in the tray that are so loosely dimensioned as an inside diameter, compared to the outside diameter of a held tip, that the tips are likely to slide horizontally within the apertures to the extent that they will not properly line up with the probe, even when the tip in question is nominally located at the station for probe pickup. That is, the apertures provide such a degree of sliding tolerance (are so much larger than the held tips' outside diameter) that as the tips are carried to the probe station, they will end up displaced out of vertical alignment with the probe, beyond the degree of displacement that the probe can tolerate. As a result, some mechanism is needed to realign the slid tips, and this invention addresses that problem.

SUMMARY OF THE INVENTION

It is the object of the present invention to provide a reliably operating device of simple design for moving and aligning a pipette tray in an analyzer. The object is obtained, in one aspect of the invention, by apparatus for aligning a tray of pipette tips into a proper position at a pickup station that includes an aspirator probe mounted to descend to pick up a tip, comprising:

means for moving tips to the station while being carried in a tray having a degree of horizontal sliding freedom that is greater than the horizontal margin of error in mating the probe with a tip, means for stopping at least one of the tips at the station while still in the tray, the stopping means including means for locating the one tip at a known location in the tray but at a discrete angle off of vertical, and control means for reorienting the located one tip so as to be substantially aligned with the vertical and with the probe.

In another aspect of the invention, the object is attained by apparatus for aligning a tray of pipette tips into a proper position at a pickup station that includes an aspirator probe mounted to descend to pick up a tip, comprising:

moving means for supporting a tray of pipette tips and for moving them in a first direction towards the station, the tips being mounted in apertures in the tray that provide a degree of sliding tolerance in a horizontal plane that is larger than can be accepted by the probe trying to pick up a tip from the tray, drive means for advancing the moving means in the first direction, stop means at the station for stopping a tray but not the moving means from advancing and for pushing an advancing tip back into contact against the backside of the corresponding aperture in a tray that is opposite to the first direction, to define a known position of the tip, a sensor at the pickup station for sensing the presence of a stopped tray and for generating a signal effective to stop the moving means, and control means for orienting the pushed-back tip so as to be vertical while still in contact with the contacted side of the aperture, and vertically aligned with the aperture, so that the aspirating probe will properly mate with the pushed-back tip when the probe descends to engage the tip.

In another aspect of the invention, the object of the invention is attained by a method of aligning a pipette tip in position to be picked up by an aspirating probe at a pickup station, comprising the steps of:

a) placing a tip into a support tray in a hole having a width that is larger than the width portion of the tip within the hole by an amount that is greater than the pickup tolerance of the probe, b) advancing the tip in a first direction to a sensor and a stop means at the station, c) stopping the tip with the stop means so that the tip is pushed to the backside of its hole that is opposite to the first direction, and d) orienting the pushed-back tip to be vertical and still in contact with the backside of the hole, and aligned under the probe, so that the tip is in the desired position for pickup by the probe.

In preferred examples, the invention provides for a pipette tray resting on the continuous movement means driven by the stepper motor first to be moved towards the stop member and after reversal of the stepper motor returned to its processing position by one or more indexing steps in the opposite direction. In this way, each pipette is reliably and exactly aligned in its processing station.

Moreover, the sensor means is preferably designed as an optoelectric sensor, and the pipette tray is provided with a supporting rim on both sides having apertures and partitions forming an encoding bar for the sensor means.

Further features and advantages will be apparent from an embodiment of the invention shown in the drawings as well as the following description.

DESCRIPTION OF THE PREFERRED EMBODIMENTS

Figure 1:
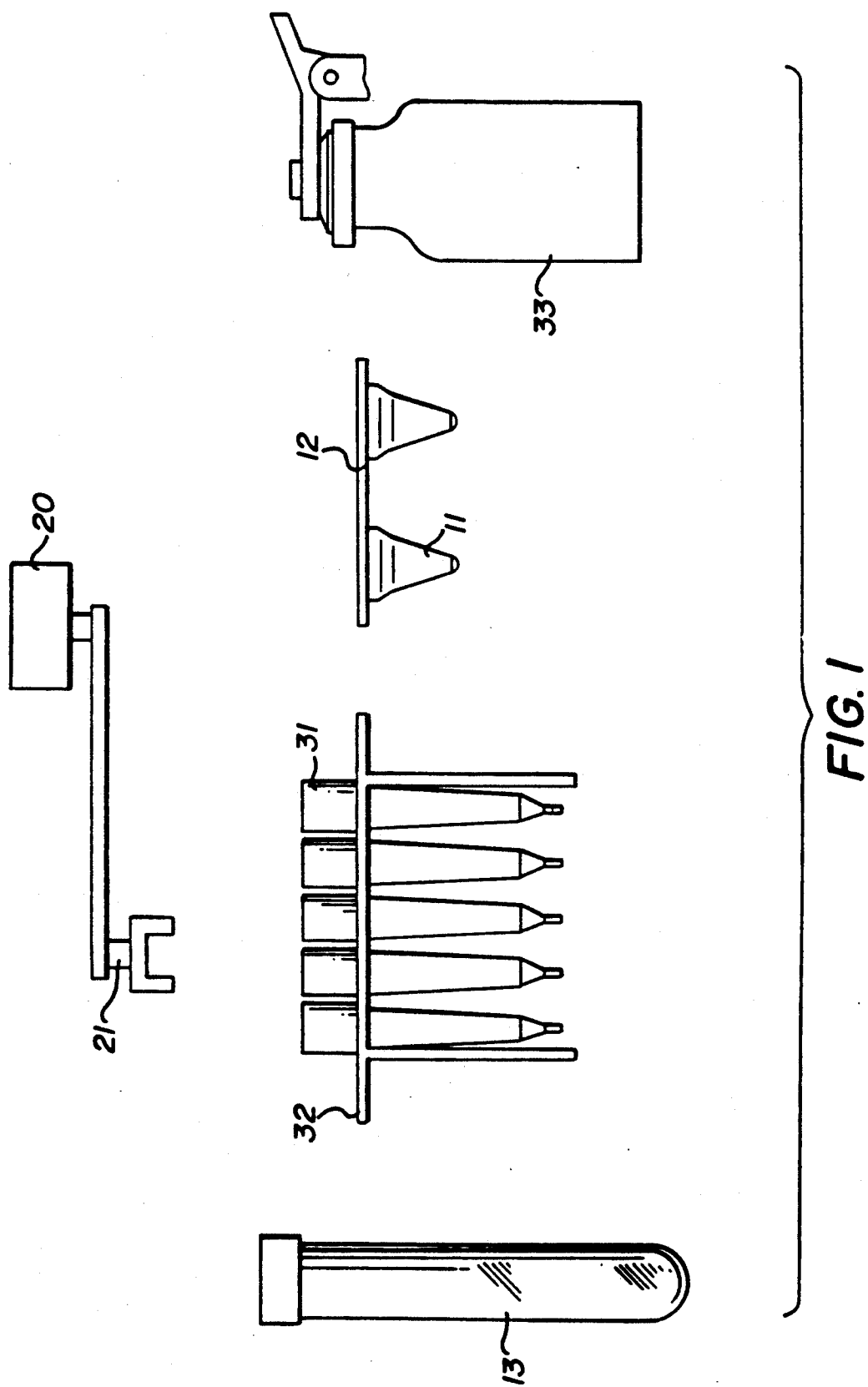
FIG. 1 shows a schematic representation of the containers, vessels, tips and the like and an aspirator used in the analyzer, the mechanisms holding each of these having been omitted for clarity.

FIG. 1 shows a schematic representation of the containers and vessels used in an analyzer for determining the properties of body fluids, e.g. blood serum.

For this case, a number of bottles 33 filled with various diluents are provided in the analyzer. The viscous body fluid in the sample tube 13 and the diluent in bottle 33 are mixed in cups 11 arranged in a cup holder 12. For this purpose, pipettes 31 are provided held for removal in a pipette tray 32. By means of a microprocessor controlled aspirator 20 including a schematically-shown proboscis 21, body fluid from the sample tube 13 and diluent from a bottle 33 can be brought to a cup 11 and mixed therein.

Figure 2A:
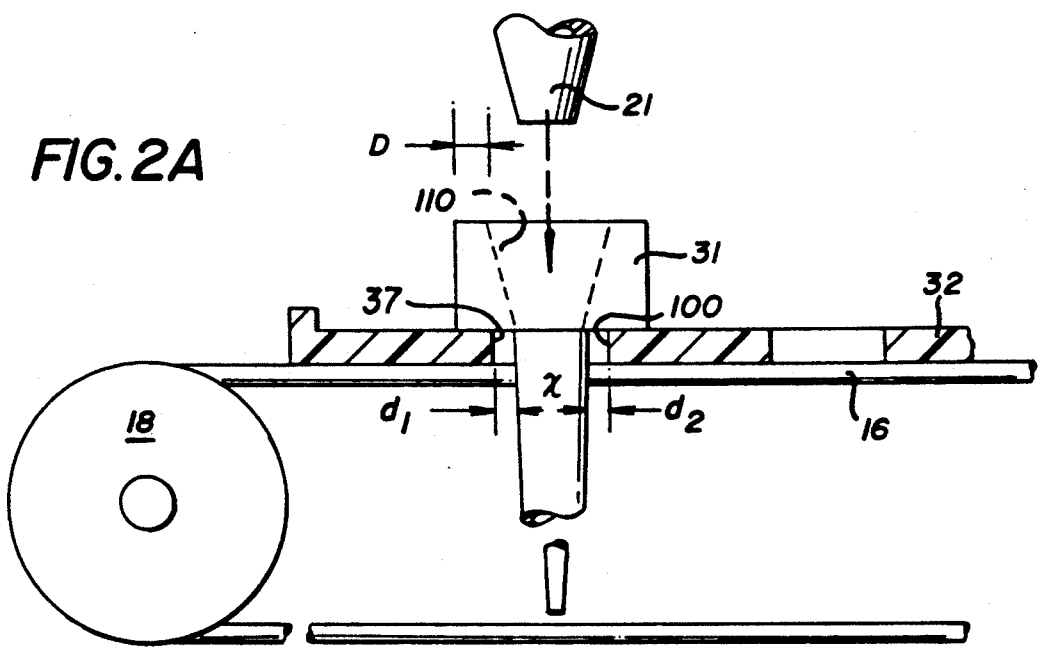
FIG. 2A is a fragmentary elevational view in section of a tray advancing towards the stopping means of the invention.
Figure 2B:
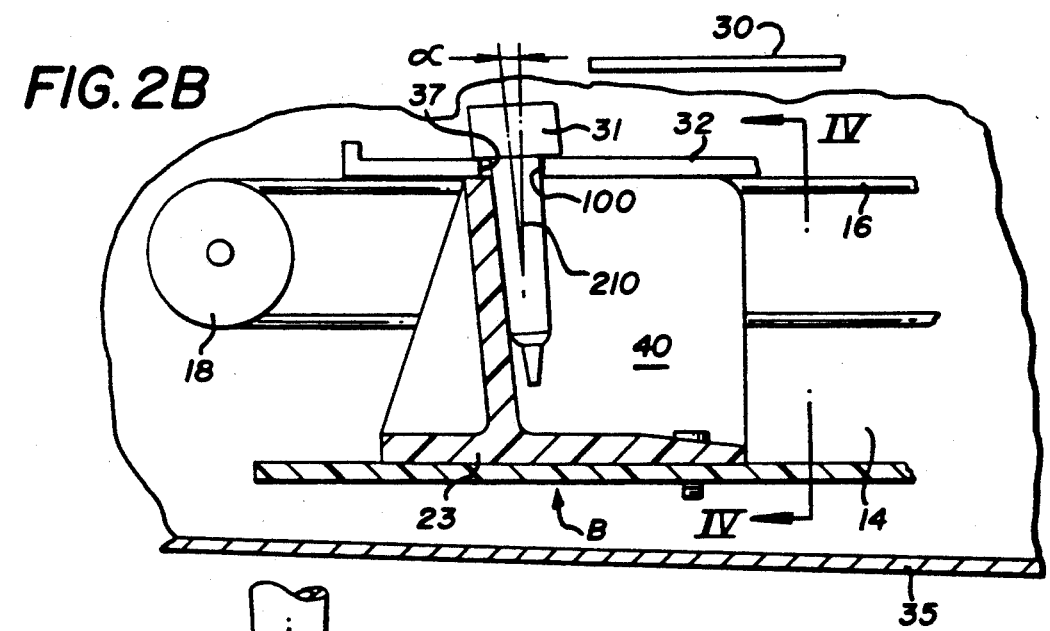
FIG. 2B is a view similar to that of FIG. 2A, but of the tray when it encounters the stopping means.
Figure 2C:
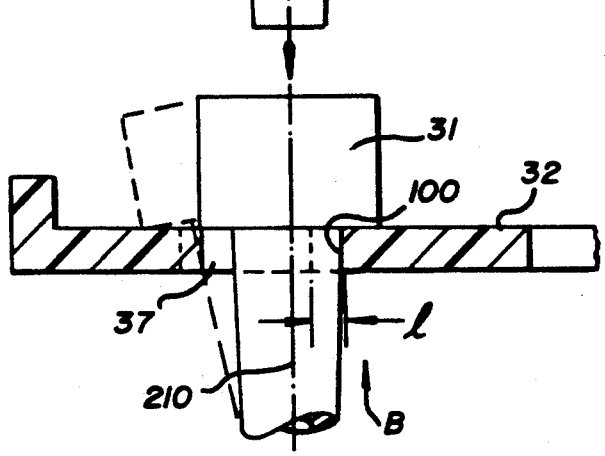
FIG. 2C is a view similar to that of FIG. 2B, but after the control means has reoriented the tip to the vertical.
Figure 3:
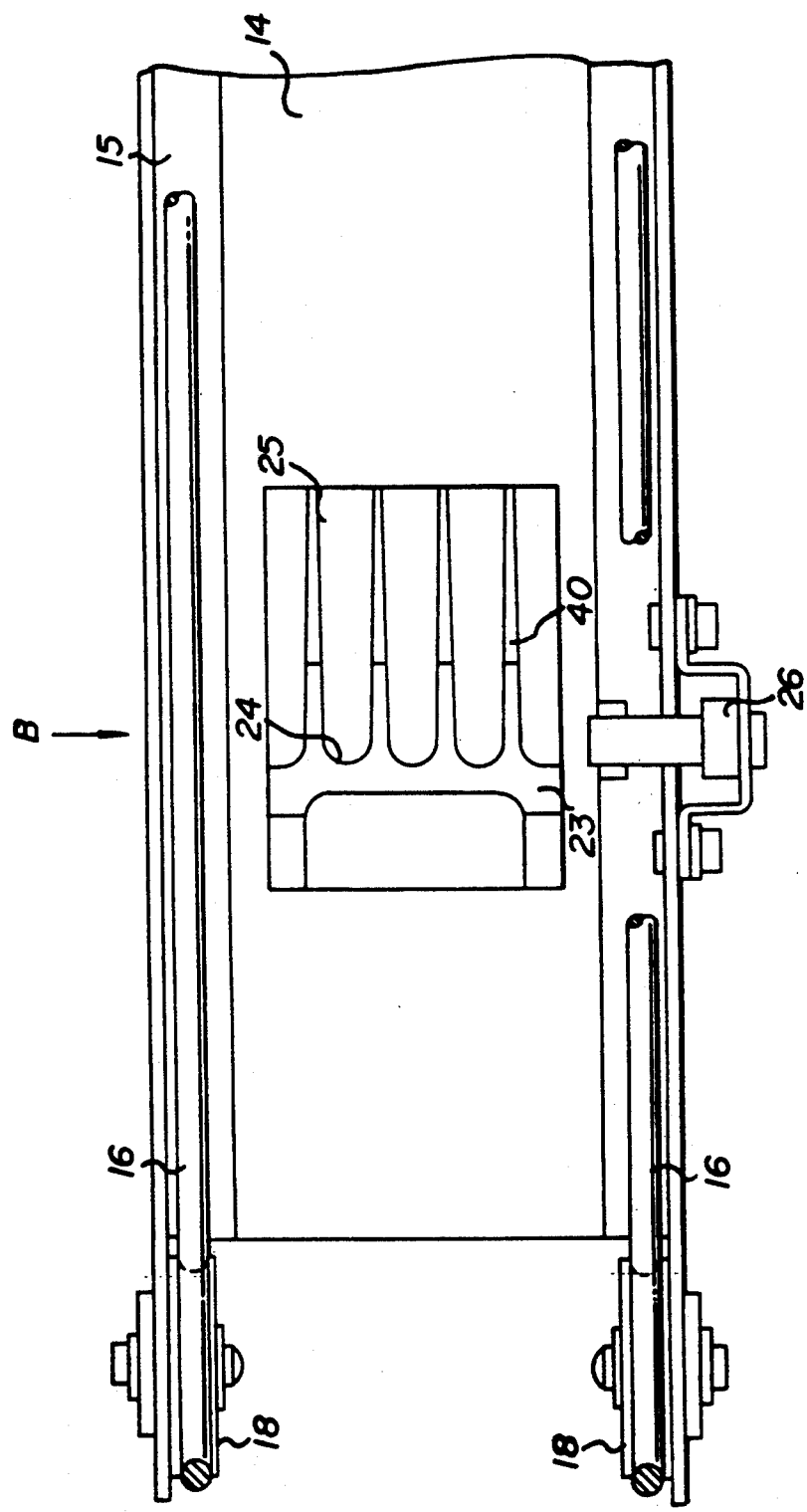
FIG. 3 is a plan view of the device of the invention.

The subject of the invention is the movement and alignment of the pipette tray 32 in a processing station B, FIGS. 2C and 3. As illustrated in the drawing, the device according to the invention includes a tray feedway comprising an elongate guide trough 14 of U-shaped cross-section extending from an input station formed at the front face of the analyzer to the interior of the apparatus.

The vertical legs of guide trough 14 are both provided with an outwardly oriented shoulder 15 by means of which one portion of a continuous movement means 16 is slidingly supported. The continuous movement means 16 is driven by a microprocessor controlled stepper motor 17 via pulleys 18. The stepper motor 17 is arranged in the housing such that the two continuous movement means 16 each running over a shoulder 15 are driven in synchronism. For this purpose, the stepper motor 17 is arranged beneath guide trough 14 and provided with a dual shaft 19 carrying drive pulleys 22, FIG. 4.

Within guide trough 14 a stop member 23 is mounted having a number of stop surfaces 24 associated with the pipettes 31 and being arranged normal to the direction of movement of the continuous movement means 16 and thus to a pipette tray 32. The stop surfaces 24 are adapted to the shape of pipettes 31 and located at the end of feed channels 25 separated from one another by thin walls 40 and contribute to the exact alignment of the pipettes 31 in their processing station, FIG. 3.

Preferably, stop member 23 comprises an electrically conductive material and is connected to ground through the rest of the apparatus, in a conventional manner, so that member 23 will function to discharge electrostatic charges that build up in a tray as the movement means 16 continues to push it against member 23.

Figure 5:
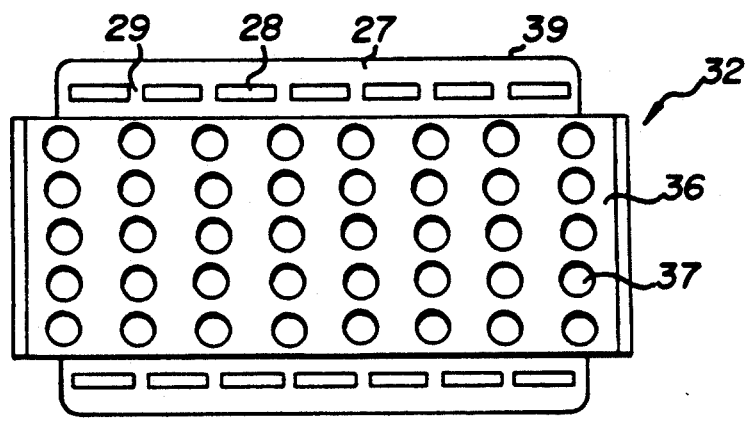
FIG. 5 is a plan view of a pipette tray used in the device.
Figure 6:
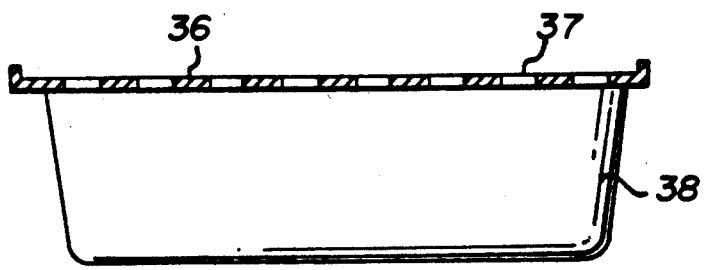
FIG. 6 is a cross-sectional side elevational view of the pipette tray according to FIG. 5.

An optoelectric sensor means 26 is arranged to one side of guide trough 14 in the area of stop member 23 which means is used for stopping the drive of belt 16 by cooperating with encoding bars 27 formed at the longitudinal rims of a pipette tray 32 and consisting of signalling slits 28 and partitions 29, FIG. 5.

At the end of the guide trough 14 located within the apparatus a return chute 35 starts which is arranged below trough 14 and extends as far as the input station at the front side of the analyzer, FIG. 2B.

A pipette tray 32 consists of a flat plate 36 having receptacles 37 for pipettes 31. The receptacles are arranged in eight rows extending normal to the direction of tray movement. Each row comprises five holes so that a pipette tray 32 can hold 40 pipettes 31.

On both sides, plate 36 is provided with a vertically extending longitudinal wall 38 the height of which is dimensioned such that the pipette tray 32 can be placed on a supporting surface without the pipette ends touching said surface. Plate 36 also features a supporting rim 39 on both sides parallel to the longitudinal wall 38 which supporting rim also comprises the encoding bar 27.

The device operates as follows:

In the input station, the pipette trays 32 equipped with pipettes 31 are placed on the continuous movement means 16 designed as belts of circular cross-section and, due to the frictional engagement between their supporting rims 39 and the belts, are driven until the first row of pipettes 31 abuts stop member 23 whereby the pipettes are tilted out of the vertical by a non-zero angle alpha, FIG. 2B. (Alpha can be, for example, about 5°.)

This "stops" tray 32, but only because the front row of tips 31 is now pushed against the backside 100 of apertures 37 in the tray, thereby fixing the location of the tip to a known surface of the tray, FIG. 2B. This solves the indeterminancy of location that otherwise exists due to the inherently sloppy fit created by the inside diameter of aperture 37 being greater than the outside diameter $\chi$ of tips 31 (measured at the part that fits inside the aperture, FIG. 2A), by an amount $d_1+d_2$. Furthermore, this excess in diameter of $d_1+d_2$ provides a degree of slippage tolerance that exceeds that allowed by probe 21, which preferably is inserted into an opening 110 (shown in phantom) of tips 31. More precisely, the degree of misalignment tolerated by probe 21 is a dimension "D", where $D<(d_1+d_2)$.

Figure 4:
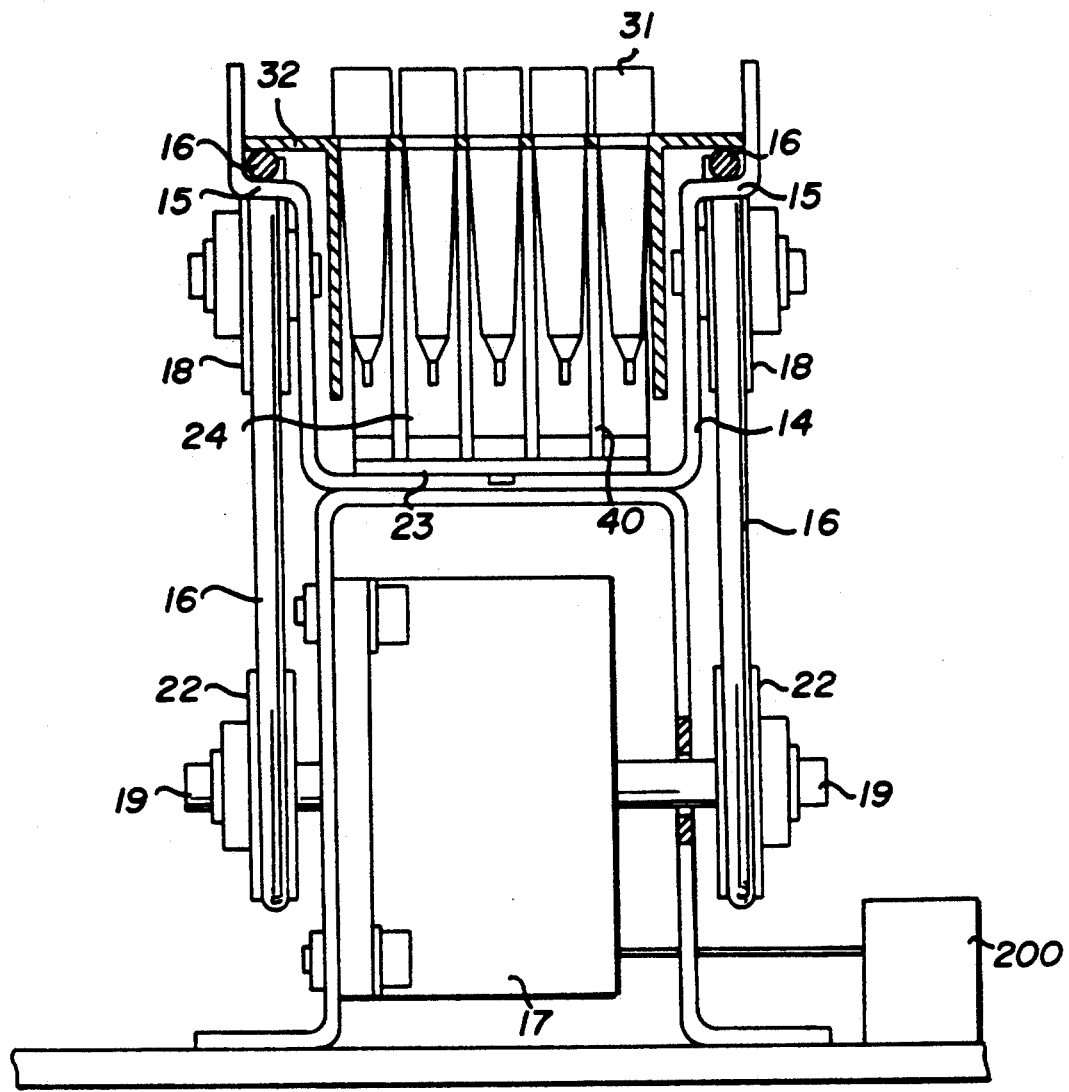
FIG. 4 is a section view taken generally in the direction of IV—IV of FIG. 2B.

Meanwhile, belt 16 continues to be driven to advance by belt pulley 18, until one of two options occurs:

a) sensor 26 senses that a slit 28 has passed but that no more have passed, so that a tray is stopped. The sensor then generates a signal to turn off pulley 18's rotation, and the tray stops trying to advance.

b) sensor 26 senses the same information as in a) above, but control means comprising a conventional microprocessor 200, FIG. 4, is programmed to allow continued advance of movement means 16 so that additional trays (not shown) will back up against the tray at station B, FIG. 2C. This ensures that no gaps exist between trays when the last tip is removed from the tray already at station B.

In either case, after movement means 16 is stopped, the aforesaid control means is operative, by its programming, to back up (in the opposite direction) belt 16 a small distance l. FIG. 2C, so that aperture 37 holding tip 31 backs up that distance. Distance l is selected to be quite small. That is, it is only large enough to allow tip 31 to tilt back into alignment with the vertical (axis 210 of tip 31 is shown as being vertical), without disturbing tip 31's contact with backside 100 of aperture 37. For example, l is preferably less than 0.5 mm, and most preferably about 0.1 or 0.2 mm, using known half-steps of the motor (preferably stepper motor 17) that drives the pulleys 18. By careful selection of the position of stop member 23 vis-a-vis the position of probe 21, the proper positioning of tip 31 directly under probe 21, FIG. 2C, is ensured.

When probe 21 descends, it presses tray 32 onto the top surface of stop member 23. Thus stop member 23 also acts as a support surface for the tray when probe 21 is engaging a tip in the tray.

Then the probe 21 engages a pipette 31 and pulls it out of the pipette tray 32. Using this first pipette 31, body fluid is removed from sample tube 13 positioned in its processing station and delivered into a cup 11 which is also positioned in its processing station. The first used pipette 31 is then thrown into a waste bin and the aspirator 20 and probe 21 remove a second pipette 31 from tray 32 in order to suck diluent from a bottle 33 by means of proboscis 21 and deliver it also to cup 11 filled with body fluid. Repeated aspiration and ejection by the proboscis 21 evenly mixes the fluids to the consistencies desired. As soon as diluted body fluid has been delivered to a dispenser which in turn delivers a predetermined quantity to a slide, the second pipette is also discarded. If there are still non-used pipettes in a row of pipette tray 32 which, however, are not required immediately, this is signalled to the microprocessor and tray 32 is moved back a predetermined amount of steps by stepper motor 17 so that the non-used clean pipettes 31 are protected by a cover 30. This avoids fouling of the pipettes 31.

Control means 200 keeps track of the tips used in a row of a tray. When the row is used up, motor 17 is turned on to advance the tray until the next row of tips stops the tray by abutting stop member 23. The sensor senses the tray has stopped, and turns off motor 17.

When all pipettes 31 have been removed from a pipette tray 32, the tray is advanced further by the continuous movement means 16 until it drops into the return chute 35, slides back automatically to the input station at the front side of the analyzer, is removed and again equipped with pipettes.

The invention disclosed herein may be practiced in the absence of any element which is not specifically disclosed herein.

The invention has been described in detail with particular reference to certain preferred embodiments thereof, but it will be understood that variations and modifications can be effected within the spirit and scope of the invention.

What is claimed is:

1. In an apparatus for aligning a tray of pipette tips in proper position at a pickup station, said apparatus comprising, said tray pipette tips and said pickup station, said tips each having a longitudinal axis and said pickup station including an aspirator probe mounted to descend to pick up a tip, the improvement comprising:
    means for moving tips to said station while being carried in said tray, said tray having means for holding said tips with said longitudinal axis in a substantially stable vertical position, said holding means having a degree of horizontal sliding freedom for said tips that is greater than a horizontal margin of error in mating said probe with a tip,
    means for stopping at least one of said tips at said station while still in said tray, said stopping means including means for locating said one tip at a known location in said tray but at a discrete angle off of vertical,
    means for sensing that the tray has stopped moving, and control means for reorienting said located one tip so as to be substantially aligned with the vertical and with said probe.

2. Apparatus as defined in claim 1, wherein said moving means comprise an endless support for supporting said tray on a support plane and means for driving said support, and said stopping means comprise a fixed vertical surface positioned below said support plane and in front of the path of the tip carried by a tray on said support.

3. Apparatus as defined in claim 2, wherein said sensing means includes a sensor for sensing when a tip and its tray have been stopped by said fixed vertical surface, said sensor being constructed to generate a signal effective to shut off said driving means when a stopped tray is sensed.

4. Apparatus as defined in claim 3, wherein said sensor is positioned to sense signalling slits in the tray carried by said support.

5. In an apparatus for aligning a tray of pipette tips into a proper position at a pickup station, said apparatus comprising, said tray of pipette tips and said pickup station, said tips each having a longitudinal axis and said pickup station including an aspirator probe to descend to pick up a tip, the improvement comprising:
    moving means for supporting a tray of pipette tips and for moving them in a first direction towards said station, said tips being mounted with said longitudinal axis in a substantially stable vertical position in apertures in the tray that provide a degree of sliding tolerance in a horizontal plane that is larger than can be accepted by said probe trying to pick up a tip from the tray,
    drive means for advancing said moving means in said first direction,
    stop means at said station for stopping a tray but not the moving means from advancing and for pushing an advancing tip back into contact against the backside of the corresponding aperture in a tray that is opposite to said first direction, to define a known position of said tip,
    a sensor at said pickup station for sensing the presence of a stopped tray and for generating a signal effective to stop said moving means,
    and control means for orienting said pushed-back tip so as to be vertical while still in contact with said contacted backside of said aperture, and vertically aligned with said aperture, so that said aspirating probe will properly mate with said pushed-back tip when the probe descends to engage said tip.

6. Apparatus as defined in claim 5, wherein said control means comprise programmed means for reversing said drive means to back up said moving means in a direction opposite to said first direction by an amount effective to (a) correct any tilt out of vertical in the pushed-back tip, caused by said stop means, without disturbing the contact of said pushed-back tip with said backside of said aperture, and (b) to position the pushed-back tip under said probe.

7. Apparatus as defined in claim 6, wherein said effective amount is less than 0.5 mm.

8. Apparatus as defined in claim 6, wherein said control means is programmed to cause said drive means to advance a plurality of trays into contact with each other and with said stop means before said signal generated by said sensor is effective to stop said moving means.

9. Apparatus as defined in claim 5, wherein said stop means comprise a barrier that is constructed and disposed to fit under the tray of tips carried by said moving means past said station, and positioned to intersect and stop the advancing of tips.

10. Apparatus as defined in claim 9, wherein said barrier includes a support surface for said tray effective to provide vertical support that opposes the force of said probe as it descends to engage a tip.

11. Apparatus as defined in claim 9, wherein said barrier is shaped to mate generally with the shape of a tip coming into contact with said barrier.

12. Apparatus as defined in claim 5, wherein said sensor is an electro-optical sensor.

13. Apparatus as defined in claim 12, wherein said sensor senses signalling slits in the tray on said moving means.

14. Apparatus as defined in claim 5, and further including in said stop means, discharge means for discharging electrostatic charges built up in an advancing tray.

15. Apparatus as defined in claim 14, wherein said discharge means comprise an electrically conductive path in said stop means extending from a point where it contacts a tray, to a ground in said apparatus.

* * * * *